US009592171B2

(12) United States Patent
Delp, II et al.

(10) Patent No.: US 9,592,171 B2
(45) Date of Patent: Mar. 14, 2017

(54) HYPERBARIC CHAMBER SYSTEM AND RELATED METHODS

(75) Inventors: William H. Delp, II, Lake Worth, FL (US); Rui M. Barbosa, Lake Worth, FL (US)

(73) Assignee: UNDERSEA BREATHING SYSTEMS, INC., Lake Worth, FL (US)

( * ) Notice: Subject to any disclaimer, the term of this patent is extended or adjusted under 35 U.S.C. 154(b) by 292 days.

(21) Appl. No.: 13/593,721

(22) Filed: Aug. 24, 2012

(65) Prior Publication Data

US 2013/0047988 A1 Feb. 28, 2013

Related U.S. Application Data

(60) Provisional application No. 61/527,259, filed on Aug. 25, 2011, provisional application No. 61/565,151, (Continued)

(51) Int. Cl.
*A61G 10/02* (2006.01)
*A61M 16/06* (2006.01)
*A61M 16/10* (2006.01)
*A61M 16/16* (2006.01)
*A61M 16/00* (2006.01)

(52) U.S. Cl.
CPC ....... *A61G 10/026* (2013.01); *A61M 16/0666* (2013.01); *A61M 16/10* (2013.01); *A61M 16/161* (2014.02); *A61M 2016/0027* (2013.01); *A61M 2016/1025* (2013.01); *A61M 2202/0208* (2013.01); *A61M 2202/0275* (2013.01); *A61M 2205/3358* (2013.01); *A61M 2205/3368* (2013.01)

(58) Field of Classification Search
CPC .................................................... A61G 10/026
USPC .................................................... 128/205.26
See application file for complete search history.

(56) References Cited

U.S. PATENT DOCUMENTS 3,369,343 A 2/1968 Robb
3,593,735 A 7/1971 Reiher
(Continued)

FOREIGN PATENT DOCUMENTS

JP 57144020 9/1982
JP 1264905 10/1989
(Continued)

OTHER PUBLICATIONS

PCT International Searching Authority:, International Search Report and Written Opinion dated May 14, 2013; entire document.

*Primary Examiner* — Steven Douglas
*Assistant Examiner* — Kathrynn Lyddane
(74) *Attorney, Agent, or Firm* — Allen Dyer Doppelt Milbrath & Gilchrist

(57) ABSTRACT

Hyperbaric chamber control system and apparatus and related methods. A system for controlling, measuring, and reporting hyperbaric chamber sessions using the partial pressure of oxygen as the lead variable. Air is gently flushed from the bottom of the chamber, upwards, and a nostril-level oxygen pickup measures oxygen concentration in the chamber. Chamber pressure and oxygen concentration values are used to calculate the partial pressure of oxygen, and the session time is adjusted so that a subject treatment accurately reflects prescribed treatment.

23 Claims, 15 Drawing Sheets

Related U.S. Application Data filed on Nov. 30, 2011, provisional application No. 61/593,591, filed on Feb. 1, 2012, provisional application No. 61/619,658, filed on Apr. 3, 2012, provisional application No. 61/609,688, filed on Mar. 12, 2012.

(56) References Cited

U.S. PATENT DOCUMENTS

| | | | |
|---|---|---|---|
| 3,727,626 A | 4/1973 | Kanwisher et al. | |
| 3,777,809 A | 12/1973 | Milde, Jr. | |
| 3,799,218 A | 3/1974 | Douglass | |
| 3,889,670 A * | 6/1975 | Loveland et al. | 128/203.12 |
| 3,930,813 A | 1/1976 | Gessner | |
| 3,976,451 A | 8/1976 | Blackmer et al. | |
| 4,022,234 A | 5/1977 | Dobritz | |
| 4,023,587 A | 5/1977 | Dobritz | |
| 4,174,955 A | 11/1979 | Blackmer et al. | |
| 4,198,213 A | 4/1980 | Mannatt | |
| 4,230,463 A | 10/1980 | Henis et al. | |
| 4,328,799 A * | 5/1982 | LoPiano | 604/23 |
| 4,421,529 A | 12/1983 | Revak et al. | |
| 4,428,372 A * | 1/1984 | Beysel et al. | 128/202.26 |
| 4,537,606 A | 8/1985 | Itoh et al. | |
| 4,560,394 A | 12/1985 | McDonald et al. | |
| 4,632,677 A | 12/1986 | Blackmer | |
| 4,681,602 A | 7/1987 | Glenn et al. | |
| 4,695,295 A | 9/1987 | Dorman et al. | |
| 4,758,251 A | 7/1988 | Swedo et al. | |
| 4,789,388 A | 12/1988 | Nishibata et al. | |
| 4,834,779 A | 5/1989 | Paganessi et al. | |
| 4,849,174 A | 7/1989 | Brandt et al. | |
| 4,860,803 A | 8/1989 | Wells | |
| 4,894,068 A | 1/1990 | Rice | |
| 4,950,315 A | 8/1990 | Gollan | |
| RE33,502 E | 12/1990 | Gollan | |
| 5,053,058 A | 10/1991 | Mirariten | |
| 5,061,377 A | 10/1991 | Lee et al. | |
| 5,069,692 A | 12/1991 | Grennan et al. | |
| 5,120,329 A | 6/1992 | Sauer et al. | |
| 5,125,937 A | 6/1992 | Sadkowski et al. | |
| 5,129,921 A | 7/1992 | Baker et al. | |
| 5,129,924 A | 7/1992 | Schultz | |
| 5,157,957 A | 10/1992 | Mettes et al. | |
| 5,158,584 A | 10/1992 | Tamura | |
| 5,169,415 A | 12/1992 | Roettger et al. | |
| 5,226,931 A | 7/1993 | Combier | |
| 5,239,856 A | 8/1993 | Mettes et al. | |
| 5,266,101 A | 11/1993 | Barbe et al. | |
| 5,284,506 A | 2/1994 | Barbe | |
| 5,302,258 A | 4/1994 | Renlund et al. | |
| 5,306,331 A | 4/1994 | Auvil et al. | |
| 5,324,478 A | 6/1994 | Mermoud et al. | |
| 5,332,547 A | 7/1994 | Olson et al. | |
| 5,355,781 A | 10/1994 | Liston et al. | |
| 5,388,413 A | 2/1995 | Major et al. | |
| 5,427,160 A | 6/1995 | Carson et al. | |
| 5,437,837 A | 8/1995 | Olson et al. | |
| 5,439,507 A | 8/1995 | Barbe et al. | |
| 5,470,379 A | 11/1995 | Garrett | |
| 5,500,036 A | 3/1996 | Kalthod | |
| 5,507,855 A | 4/1996 | Barry | |
| 5,611,845 A | 3/1997 | Delp, II | |
| 5,649,995 A | 7/1997 | Gast, Jr. | |
| 5,690,096 A * | 11/1997 | Burch | 128/204.18 |
| 5,700,310 A | 12/1997 | Bowman et al. | |
| 5,730,780 A | 3/1998 | Booth, III | |
| 5,746,806 A | 5/1998 | Aylsworth et al. | |
| 5,809,999 A * | 9/1998 | Lang | 128/200.24 |
| 6,283,123 B1 | 9/2001 | Van Meter | |
| 2002/0144683 A1 | 10/2002 | Gurnee et al. | |
| 2004/0261796 A1 | 12/2004 | Butler | |
| 2009/0038618 A1* | 2/2009 | Grauke | 128/205.26 |
| 2009/0217930 A1* | 9/2009 | Holley | E04B 1/166 |
| | | | 128/205.26 |

FOREIGN PATENT DOCUMENTS

| | | |
|---|---|---|
| JP | 3109912 | 5/1991 |
| JP | 3242304 | 10/1991 |
| JP | 3242305 | 10/1991 |
| JP | 3247502 | 11/1991 |
| JP | 4005191 | 1/1992 |
| JP | 4122414 | 4/1992 |
| KR | 10-2011-0047309 | 5/2011 |
| WO | 9426394 | 11/1994 |

* cited by examiner

90 - pO₂ setpoint
92 - chamber pressure
94 - chamber pO₂
96 - O₂ conc./vol

HYPERBARIC CHAMBER SYSTEM AND RELATED METHODS

CROSS-REFERENCE TO RELATED APPLICATION

This application claims priority from: U.S. Provisional Patent Application Ser. No. 61/527,259 filed on Aug. 25, 2011 entitled "Hyperbaric Apparatus and Method for Improved Oxygen Delivery;" Provisional Patent Application Ser. No. 61/565,151 filed on Nov. 11, 2011 entitled "Pressure Swing Adsorption Apparatus and Method for Producing Oxygen Enriched Air;" Provisional Patent Application Ser. No. 61/593,591 filed on Feb. 1, 2012 entitled. "Hyperbaric Chamber Control System Apparatus and Related Methods;" Provisional Patent Application Ser. No. 61/619,658 filed on Apr. 3, 2012 entitled. "Hyperbaric Chamber Control System, Apparatus, and Related Methods;" and Provisional Patent Application Ser. No. 61/609,688 filed on Mar. 12, 2012 entitled "Apparatus and Related Method for Continuously Sampling a Hyperbaric Chamber Atmosphere." The contents of all of these provisional applications are incorporated by reference herein.

FIELD OF THE INVENTION

The present invention relates to the field of hyperbaric chambers and, more particularly, to systems and methods of controlling hyperbaric chamber sessions and measuring hyperbaric chamber treatment.

BACKGROUND

General Background

Monoplace Hyperbaric Chambers are pressure vessels intended for human occupancy with the capacity of fully enclosing one single person for the purpose of submitting the subject to an oxygen treatment at pressure higher than 1 atmosphere absolute (ATA). Such chambers have in the past been provided with mechanical and/or electromechanical means of supplying oxygen at increasingly higher concentrations and pressure to the subject.

A hyperbaric treatment typically consists of three phases: pressurization, maintenance, and depressurization. In monoplace hyperbaric chambers, initiate the pressurization phase, a subject is placed in the chamber and the chamber door is closed. The chamber at that point is full of atmospheric air. Oxygen is supplied to the chamber at a relatively high flow rate and the chamber atmosphere is vented at a slightly lower rate, thereby causing the pressure in the chamber to increase at a pre-set rate.

Once chamber pressure reaches prescribed oxygen pressure value, the chamber pressure is maintained with a constant supply of oxygen and chamber atmosphere is vented at the same rate—this is the maintenance phase, also known as treatment plateau.

Once the prescribed, session time elapses, the chamber is depressurized and the subject is removed from the chamber.

Current state of the art chamber sessions are controlled by chamber pressure and time, and do not take into consideration the actual oxygen concentration level variation from 21% to the desired 100% within the chamber atmosphere during the session, resulting in a treatment dosage that is, at best, an approximation of the inspired oxygen percentage.

The laws of physics define that the pressure of any non-reacting gas mix results from the addition of the pressures of its components—this is known as Dalton's law. The pressure of an individual gas component in a mixture of gasses is referred to as that gas's partial pressure. The pressure of a gas mixture is the sum of the partial pressures of the individual components of the gas mixture.

This law is of the utmost importance when considering the chemical and physiological effects of gases on mammalian systems. Atmospheric air contains roughly 20.9% $O_2$. At sea level and standard humidity and temperature, the partial pressure of the $O_2$ component is approximately 0.209 ATA. The remaining balance of the air pressure equaling approximately 0.791 ATA consists of the sum of the partial pressures of the balance of the air's components, primarily nitrogen, but also argon, carbon dioxide, and all other trace gases.

As a functional example, the air at the peak of a Himalayan mountain has most probably the same percentage of each component, however, because the atmospheric pressure at altitude is substantially lower, so are the partial pressures of the air's components. Most mountaineers require a personal oxygen supply at these elevated altitudes because the partial pressure of oxygen at altitude may approach the 0.14 ATA critical range, which is inadequate for a human's metabolic needs. In general, air becomes hypoxic once the ambient pressure is low enough to result in an $O_2$ partial pressure ($pO_2$) of less than 0.18 ATA. If the $pO_2$ decreases to 0.14 ATA, humans quickly become hypoxic and may die after just a short period of time. On the other hand, air becomes hyperoxic when the ambient pressure creates a $pO_2$ exceeding 0.23 ATM.

Reverse examples can be given and illustrated with SCUBA diving, wherein humans are subjected to elevated pressures. For example, when breathing pure oxygen, a subject is limited to the maximum depth of 6 meters (18 Ft) because the oxygen partial pressure at this depth is 1.6 ATA, corresponding to a $pO_2$ value considered to be the maximum for underwater activities, for the elevated $pO_2$ can potentially cause central nervous system toxicity resulting in convulsions, which would likely be deadly underwater. The same principle dictates that approximately 65 meters (~213 ft.) is the maximum depth for subjects breathing regular air (~21% $O_2$), for at this depth, the $pO_2$ is the same as breathing pure $O_2$ at 6 meters.

The above examples serve the purpose of illustrating that the physiological effects of oxygen depend on the respective $pO_2$ and not on the percentage of $O_2$ in the breathing gas mix alone.

Hyperbaric chambers (or simply "chambers") are used for medical purposes to reduce and/or eliminate numerous diseases and ailments. Without exception, all currently manufactured monoplace hyperbaric chambers using full body oxygen pressurization have a manual or manual/automatic control system. In all known cases, the hyperbaric session is controlled, by two parameters: session time and chamber absolute pressure which are prescribed by an MD. In these cases, session time (also referred to as treatment time) is defined as the time counted from the start of chamber pressurization to start of chamber depressurization. Oxygen pressure is often confused with absolute pressure of the chamber.

Referring to FIG. 1, this graph exemplifies what a physician may prescribe in the prior art for a subject: 60 minutes at 2 ATA $O_2$. This prescription is represented by the shaded area of the graph in FIG. 1.

FIG. 2 illustrates the theoretical effective portion of the prior art hyperbaric treatment of FIG. 1. Once the chamber door is closed and the pressurization cycle initiated, the treatment session clock starts. The operator starts the pressurization cycle at the same time that an exhaust valve is opened to allow for the flushing of the initial volume of air in the chamber.

FIG. 3 illustrates a chamber session, as practiced in the prior art, but additionally highlighting the actual value in the session time frame. As illustrated, in excess of minutes are required to reach approximately 96% oxygen concentration, which is close to ⅓ of the total session time. At 2 ATA and 95% concentration, the $pO_2$ is merely 1.9 ATA and not the prescribed 2 ATA of $pO_2$.

Trend analysis indicates that several hours would be necessary to reach the 2 ATA of oxygen pressure prescribed by the physician, which is well past the end of the prescribed session, assuming a prescription for 1 hour at 2.0 ATA $O_2$.

Additionally, the time frame before the chamber atmosphere reaches the level of 95%, oxygen concentration is fully counted as session time even though during the first 20 minutes of the session the oxygen partial pressure is clearly below the prescribed value.

Treatment efficacy also depends on chamber size, for a smaller chamber will arrive at acceptable levels of oxygen concentration, more quickly than a larger chamber, same flow rate provided, yet this is a variable not accounted for. When the chamber is first used it contains an amount of ambient air equal to the chamber internal volume, but when the subject is placed in the chamber, the air volume displaced by the subject is removed from the chamber. Therefore, the chamber possesses an air volume equal to its internal volume minus the volume displaced by the subject and any introduced equipment. This volumetric variation is ignored in traditional chamber treatments.

Oxygen flow rate is also currently used as means to control the chamber inner temperature and humidity. Given that gasified liquid oxygen is intrinsically cold, a chamber operator may opt to use a lower flow rate in colder days than in warmer days. This affects the rate at which the original air volume is flushed out and introduces yet another unknown variable in knowing the actual oxygen percentage in the inspired gas.

Overall, as illustrated by FIG. 3, at best the subject only receives approximately ⅔ of the treatment prescribed by the physician and the prescribed $pO_2$ is unlikely to ever truly be achieved.

There is a need for a hyperbaric chamber control system that enables a subject to receive an accurate hyperbaric treatment, as prescribed by a physician.

Pressure Swing Adsorption Background

Current hyperbaric chambers often lack portability and site compliance standards are difficult to meet due to the presence of liquid oxygen. The storage of liquid oxygen represents a very high risk of explosion and fire, and the premises must be explosion proof in most jurisdictions. Since liquid oxygen is also not readily available in many areas where hyperbaric treatments are required, such as seafaring vessels, remote locations, and conflict zones, one embodiment of the present invention utilizes a pressure swing adsorption (PSA) device and method to enrich air with oxygen for use in the present embodiments of hyperbaric control.

Pressure swing adsorption (PSA) processes rely on the fact that gases under pressure tend to be attracted to solid surfaces, or adsorbed, when under pressure. The PSA oxygen enrichment process relies on a material called zeolite to remove nitrogen from ambient air. Zeolite refers to the family of aluminosilicate minerals having microporous structures capable of loosely binding with a variety of cations. Zeolite is used in oxygen enrichment, as it adsorbs nitrogen when subjected to a high pressure, yet releases the absorbed nitrogen when the pressure drops.

The PSA process works by feeding ambient air into a pressurized chamber containing zeolite. The higher the pressure within the zeolite chamber, the more gas is adsorbed. When the pressure is reduced, the gas is released. PSA processes can be used to separate gases in a mixture because different gases tend to be attracted to different solid surfaces more less strongly. If a gas mixture such as air (21% $O_2$, 78% $N_2$) is passed, under pressure, through a tower containing an adsorbent bed that attracts $N_2$ more strongly than it does $O_2$, a large portion of the $N_2$ will stay in the bed, and the gas leaving the tower will contain approximately 94% $O_2$. When a bed in the first tower reaches the end of its capacity to adsorb $N_2$, the bed can be regenerated by reducing the pressure, thereby releasing the adsorbed $N_2$. It is then ready for another cycle of producing oxygen enriched air (OEA).

To generate purified $O_2$ from air, $N_2$ from the air is absorbed by zeolite while the $O_2$ is further passed through to a storage tank. When the zeolite is saturated (so it can no longer effectively absorb $N_2$), the chamber is depressurized. When the chamber is in the depressurized state, the N is released by the zeolite and vacates the system. The chamber is than re-pressurized and the cycle is repeated to generate purified $O_2$.

SUMMARY

The present invention is directed to a method for controlling a hyperbaric chamber session. A first embodiment comprises the steps of: measuring the duration of a chamber session; measuring the internal pressure of the hyperbaric chamber; adding oxygen to the hyperbaric chamber; pressurizing the hyperbaric chamber; measuring oxygen concentration in the hyperbaric chamber; calculating the partial pressure of oxygen in the hyperbaric chamber; and maintaining the partial pressure of oxygen in the hyperbaric chamber at a predetermined level by adjusting at least one of the pressure or the amount of oxygen in the hyperbaric chamber.

In any described embodiment, measuring the duration of the session is initiated after the step of flushing air from the hyperbaric chamber until the oxygen concentration level reaches about 87%, followed by chamber pressurization with oxygen until the prescribed pO2 is reached. The total time necessary to provide a subject a prescribed hyperbaric chamber treatment dose is also calculated by the system.

In a second embodiment of the invention, the hyperbaric chamber is flushed by introducing oxygen proximate a bottom region of the hyperbaric chamber, preferably the head end, and exhausting the hyperbaric chamber atmosphere proximate a top region of the hyperbaric chamber, preferably the foot end.

In any described embodiment, the oxygen concentration is measured proximate the subject's nostrils, using for example an oxygen pickup tube supported by a user's ears.

In a third embodiment of a method of hyperbaric chamber treatment of a subject in need thereof, the method comprises steps of: placing the subject in a hyperbaric chamber; sealing the hyperbaric chamber; adding oxygen to the hyperbaric chamber; measuring pressure of the hyperbaric chamber; measuring the concentration of oxygen in the hyperbaric chamber; calculating partial pressure of oxygen in the hyperbaric chamber; pressurizing the hyperbaric chamber; measuring the time in which the subject is in the hyperbaric chamber at the prescribed pO2; and maintaining the partial pressure of oxygen at a predetermined level by adjusting at least of the chamber pressure and the concentration of oxygen in the hyperbaric chamber. This method may further comprise the step of defining a desired hyperbaric chamber treatment dose.

A fourth embodiment of the method of hyperbaric chamber treatment further contemplates the step of flushing the hyperbaric chamber by introducing oxygen proximate a bottom head end region of the hyperbaric chamber and exhausting the hyperbaric chamber proximate a top foot end region of the hyperbaric chamber. A timing device is used to measure the time in which the subject is in the hyperbaric chamber (at prescribed pO2), and is started after the (the prescribed pO2 is reached).

The invention is also directed to a hyperbaric chamber system comprising: a hyperbaric chamber with a pressure transducer for measuring pressure inside the hyperbaric chamber and an oxygen transducer measures the concentration of oxygen inside the hyperbaric chamber. A valve with the hyperbaric chamber regulates the pressure inside the hyperbaric chamber, and a hyperbaric chamber control comprises a central processing unit that calculates partial Pressure of oxygen in the hyperbaric chamber. The hyperbaric chamber control receives input signals from the pressure and oxygen transducers and outputs signals to adjust the valve so to maintain the partial pressure of oxygen at a prescribed level.

A second embodiment of the hyperbaric chamber system further comprises an atmosphere pickup for sampling the oxygen inside the hyperbaric chamber, wherein the pickup is connected to the oxygen transducer. In one embodiment, the atmosphere pickup is situated proximate a subject's nostrils.

A third embodiment of the hyperbaric chamber system further comprises an inlet proximate a bottom region of the hyperbaric chamber, as well as an outlet proximate a top region of the hyperbaric chamber, the outlet for flushing gas from the hyperbaric chamber.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION

In the Background of the Invention above, in this section, and in the accompanying drawings, reference is made to particular features of the invention. It is to be understood that the disclosure of the invention in this specification includes all possible combinations of features. For example, where a feature is disclosed in the context of particular aspect or embodiment of the invention, that feature can also be used, to the extent possible, in combination with and/or in the context of other aspects and embodiments of the invention, and in the invention generally. This invention may, however, be embodied many different forms and should not be construed as limited to the embodiments set forth herein.

Hyperbaric Chamber Control

In view of the foregoing background, it is therefore an object of the present invention to provide a hyperbaric chamber control system and method of chamber control.

It is an object of the present invention to provide a hyperbaric chamber control system that utilizes the $pO_2$ as the primary variable with which to control hyperbaric chamber session to enable accurate chamber session oxygen dosing to the subject.

It is an object of the present invention to utilize $pO_2$ as the primary variable to control a chamber treatment so a subject receives an accurate physician-prescribed hyperbaric oxygen exposure.

Since a human's physiological response to a hyperbaric chamber treatment is exclusively linked to the $pO_2$ at which the subject is exposed during treatment and to respective session time, the present invention is directed to hyperbaric treatments utilizing a system to measure and control the $pO_2$ of a chamber session.

For purposes herein, "oxygen" means any gaseous form of the oxygen element with concentration levels appropriate for use in a hyperbaric chamber, which are known in the art. The source of oxygen utilized herein is from liquid or gaseous sources.

Figure 1:
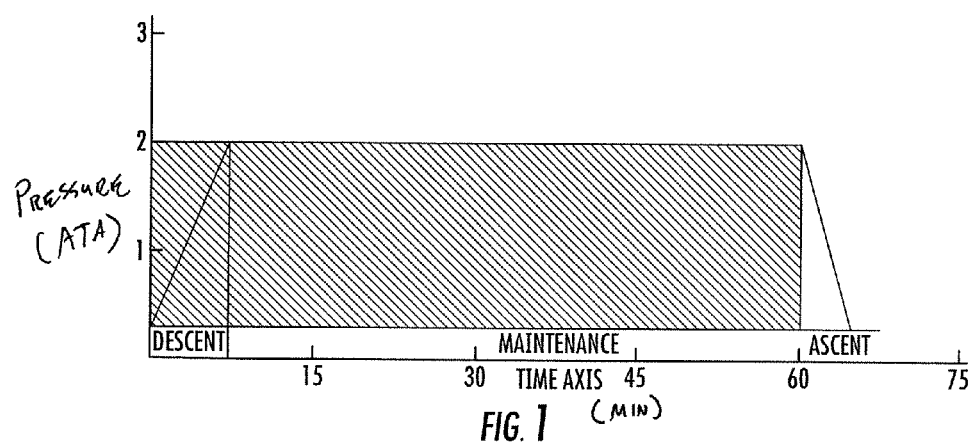
FIG. 1 is a graph illustrating an example of what a physician may have described in the prior art as a hyperbaric treatment, the underlying assumption being that the subject is receiving 100% oxygen from the moment of pressurization.
Figure 2:
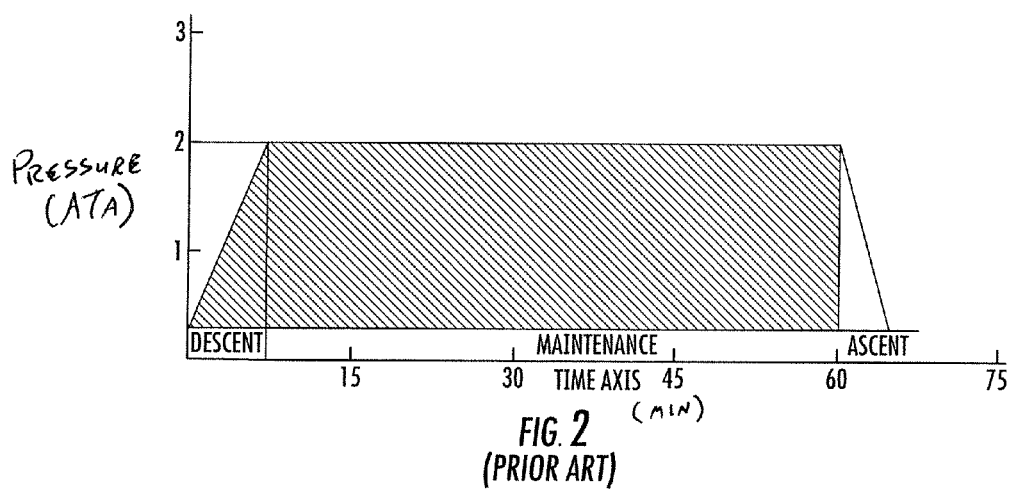
FIG. 2 is a graph illustrating the theoretical effective portion of the hyperbaric treatment illustrated in FIG. 1 as practiced in the prior art.
Figure 3:
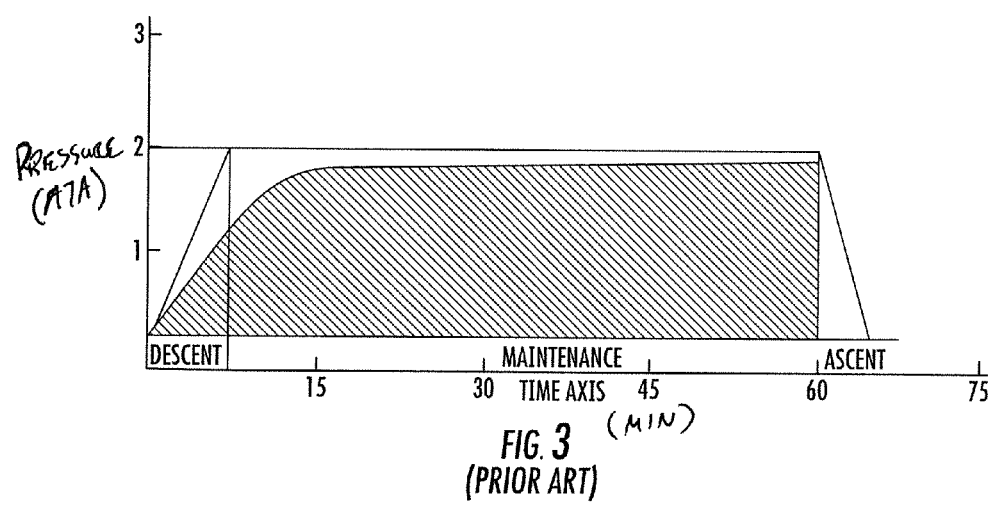
FIG. 3 is a graph illustrating recorded data of the hyperbaric treatment illustrated in FIG. 1 as practiced in the prior art, but having the content highlighted for clarification purposes.
Figure 4:
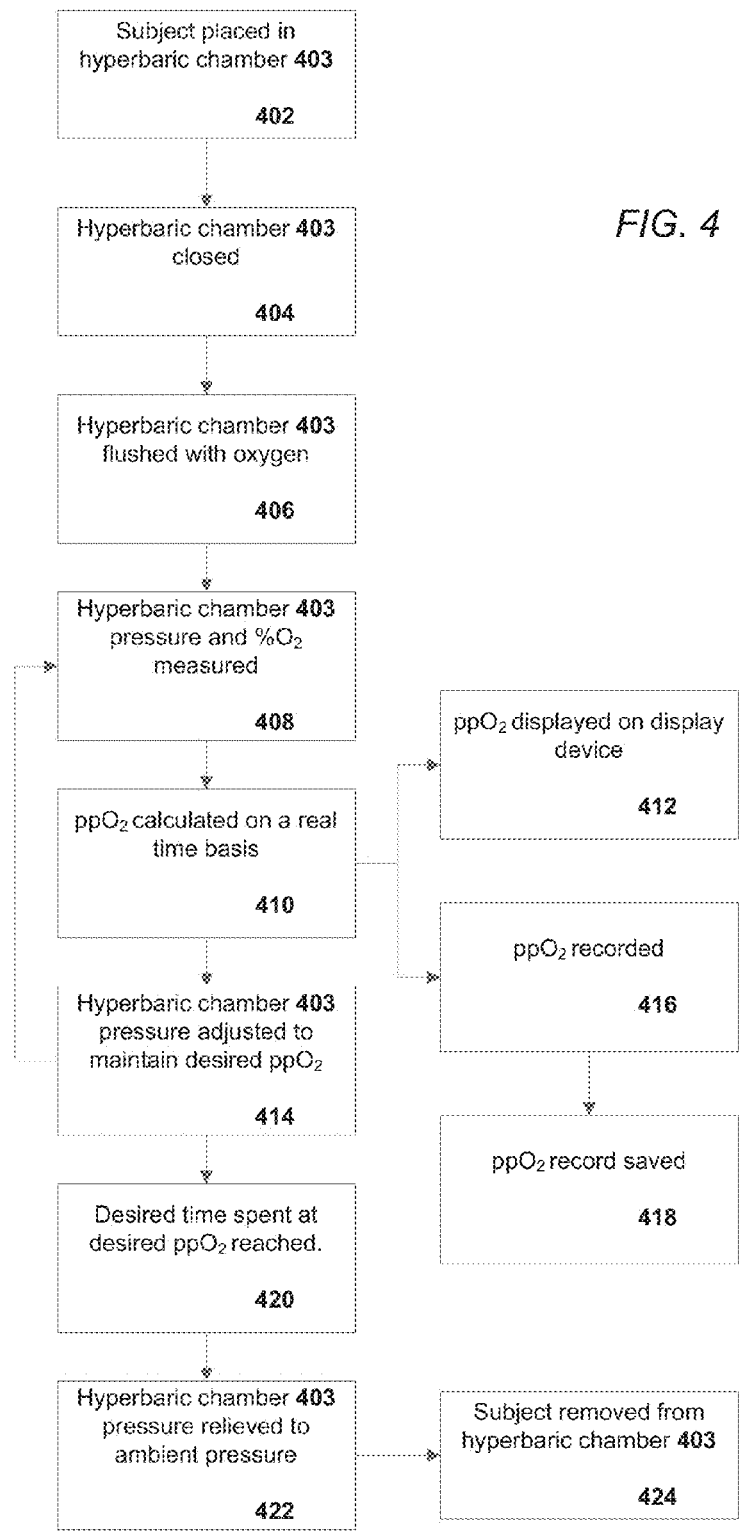
FIG. 4 is a flow chart illustrating one embodiment of the steps of a hyperbaric chamber session of the present invention.
Figure 4A:
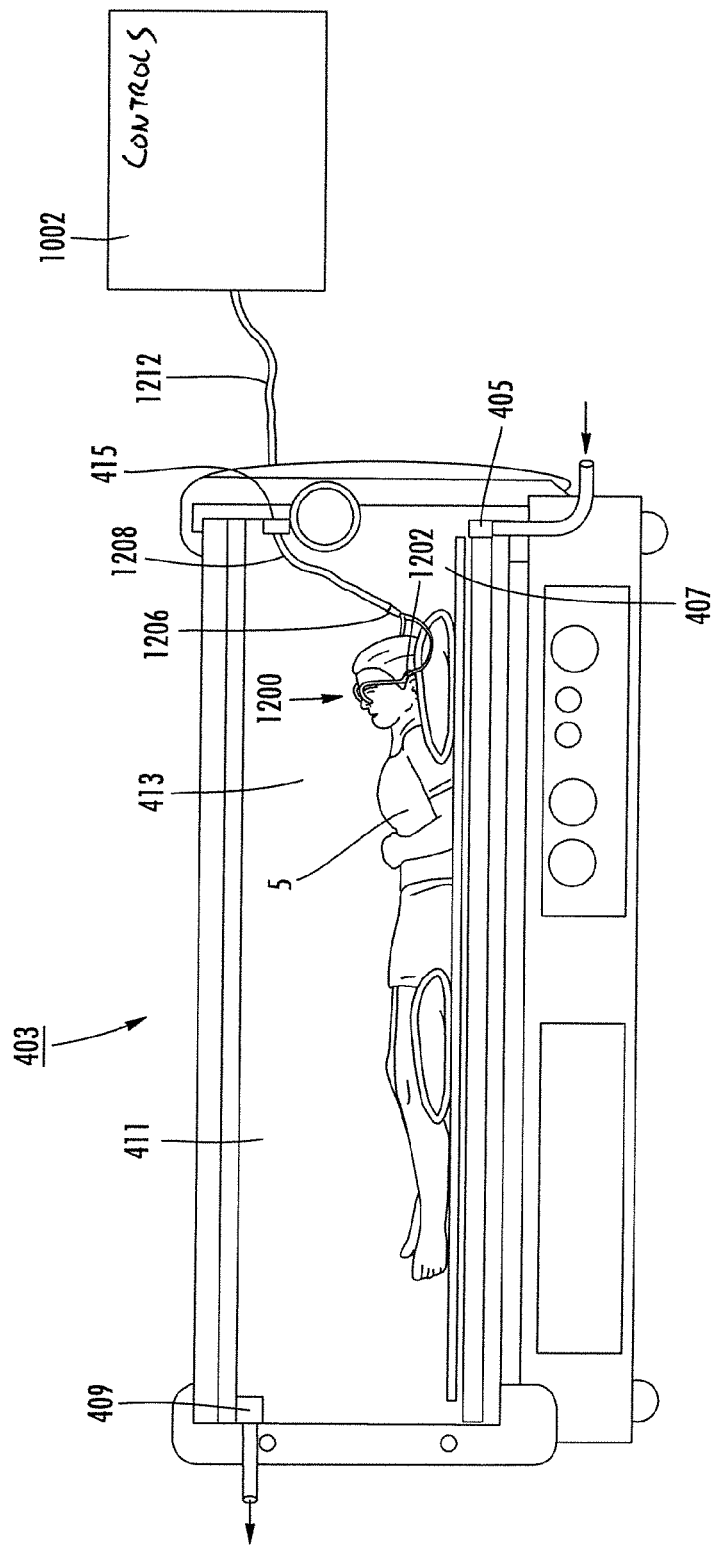
FIG. 4a illustrates a hyperbaric chamber of the present invention.

Referring to FIGS. 4 and 4a, once a subject is placed 402 in a hyperbaric chamber 403 and the chamber 403 is closed by sealing 404, the chamber 403 is flushed with $O_2$ at a relatively slow flow rate, to minimize turbulence 406. In a preferred embodiment, the desired flow rate does not increase the chamber pressure past about 2 PSIG. $O_2$ is heavier than air (1.429 Kg/m3 versus 1.225 Kg/m3), so the chamber 403 is filled through an inlet 405 proximate the bottom 407 of the chamber 403, while residual air is vented from the chamber 403 using a vent 409 proximate on the top side 411 of the chamber 403. This reduces turbulence, creating a quasi laminar flow of $O_2$, from the bottom 407 to the top 411 of the chamber 403. The chamber pressure and percentage of $O_2$ in the chamber are measured continuously 408. Based on these measurements, the $pO_2$ is calculated 410 multiple times each second. Once the $O_2$ concentration reaches at least about 87% by volume at the subject's nostril level, chamber pressurization starts. This is in contrast with most current practice, because current practice is to start pressurization at 21% oxygen concentration. Other concentration values can also be used and the system, as contemplated by current invention, calculates and administers the oxygen dosage to which a subject is subjected until the desired $_pO_2$ value is reached as subpar dosage. As soon as the $_pO_2$ reaches the prescribed level, the chamber session timer starts and the session enters the maintenance cycle during which the chamber pressure is continuously adjusted to make up for the continuously increasing $O_2$ concentration so to maintain the desired value 414. Alternatively, the session timer could be started once the $_pO_2$ reaches 1.5 ATA, which is a value defined by many physiologists as marker of the start of hyperbaric oxygen conditions. The $_pO_2$ is displayed on a display device for 412 a chamber operator, and recorded 416 and saved 418. The $_pO_2$ data are saved on a computer, computer network, computer media, paper printout, or any other means of saving data known in the art. Other variable and conditions are also saved, not limited to, subject information, subject chamber temperature, chamber $CO_2$ chamber pressure, humidity level, subject biometric data, and any other variables, or conditions known in the art.

Figure 5:
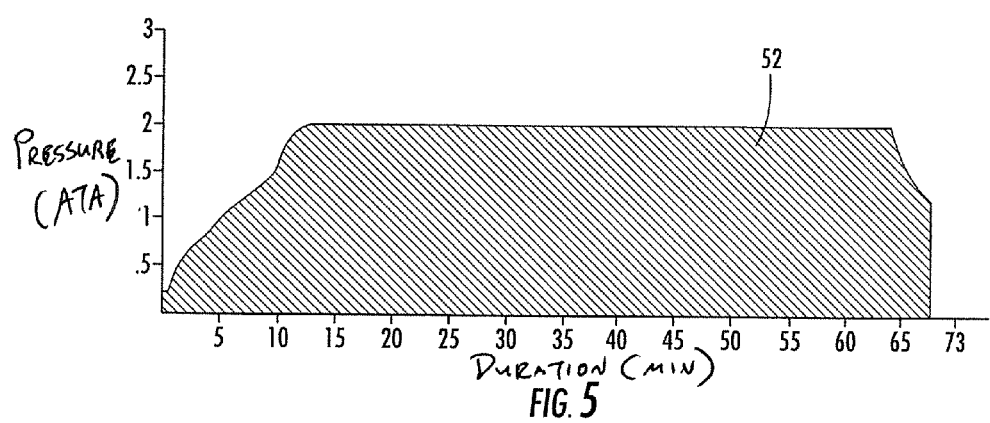
FIG. 5 is a graph illustrating the measured $pO_2$ of an hyperbaric chamber session of the present invention controlled by $pO_2$ as opposed to chamber absolute pressure.

FIG. 5 illustrates the calculated 410 (FIG. 4) and displayed 412 (FIG. 4) $_pO_2$ of an example chamber session. As oxygen starts accumulating in the bottom of the chamber, the oxygen slowly fills the chamber, moving upwards towards the subject's face. Oxygen concentration is checked on a real time basis with a sample pickup 1200 proximate the subject's nostril level. The highlighted area 52 indicates the integral of the session $pO_2$ curve from the start of a session to the end of a session and it represents the actual oxygen dosage to which a subject is exposed at the desired/prescribed $pO_2$.

Figure 6:
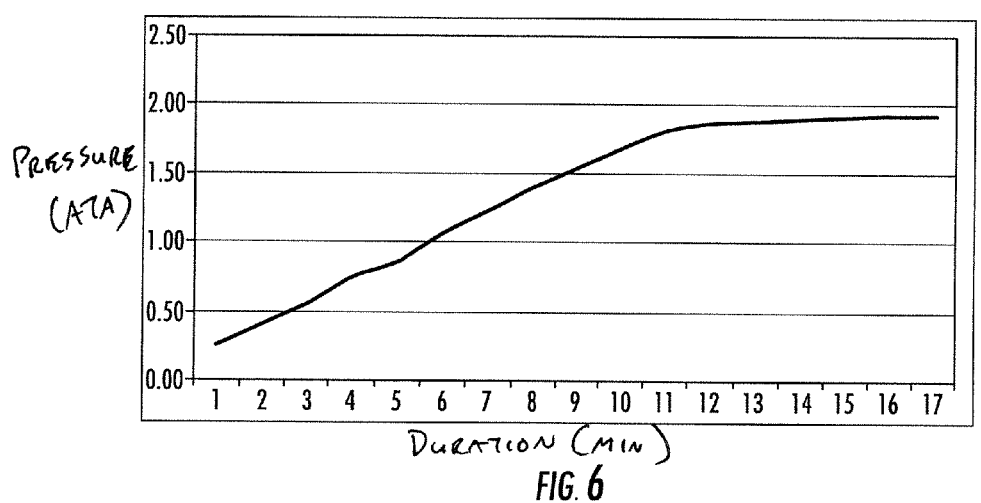
FIG. 6 is a graph illustrating the actual $pO_2$ measurements of a conventional prior art chamber session, as shown in FIG. 3.

In contrast, FIG. 6 is a graph that illustrates a hyperbaric session utilizing the conventional constant $O_2$ flow method to pressurize the chamber. The y-axis represents $pO_2$ value development for a 2 ATA oxygen pressure prescription. The $O_2$ sample pick-up point was at subject's nostrils level and the flow rate was 440 l/min during pressurization and 360 l/min during the maintenance portion of the session. The subject's first 17 minutes of this 60 minute—2 ATA session were spent in an atmosphere with an average $pO_2$, which is well under the prescribed 2 ATA. This graph also illustrates that the subject only enters the hyperbaric portion of the treatment (hyperbaric treatments are considered to be "hyperbaric" above 1.5 ATA) 9 minutes after session start.

Figure 7:
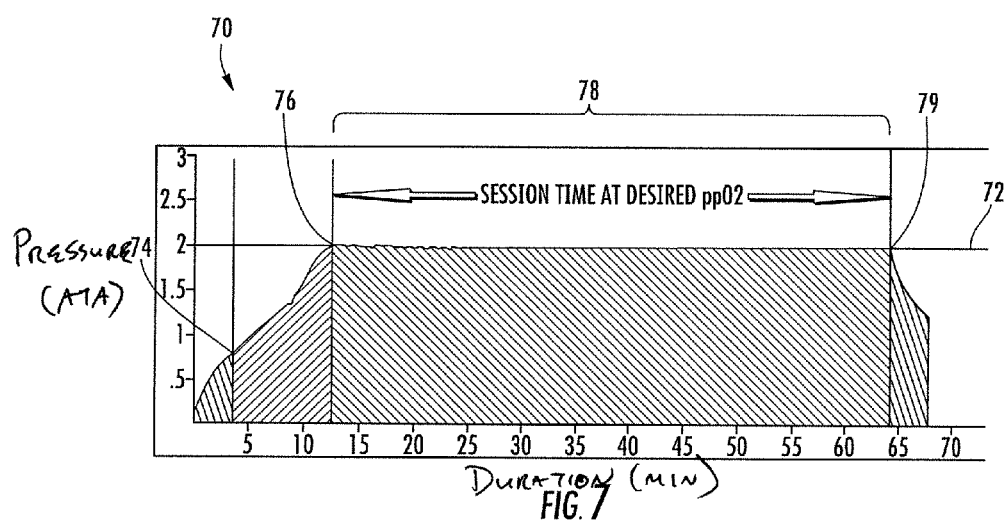
FIG. 7 is a graph illustrating the system measurements and controls related to the hyperbaric chamber session illustrated in FIG. 5.

With reference to FIG. 7, once the $O_2$ concentration by volume reaches a pre-set value, say 0.87 ATA at the subject's nostril level, the exhaust valve is closed and pressurization begins 74. This initial flushing phase of the session produces a chamber pressure of approximately 0.2 ATA, and is an important aspect of the present invention in that it reduces the potential for barotrauma injuries. The graph 70 a $pO_2$ curve illustrating that once the oxygen concentration reaches the desired value 72 (e.g. 2 ATA) the session enters into its 76 maintenance cycle 78 during which computerized controls maintain the $pO_2$ within 0.01 ATA. The $O_2$ dosage values collected at this $pO_2$ level are defined for the prescribing physician as XXX ATA-min at Y.YY ATA of $pO_2$. The $O_2$ dosage values collected during the pressurization phase are also collected and marked as subpar dosage, in order to enable physician to calculate total oxygen exposure in Oxygen Toxicity Units.

Figure 8:
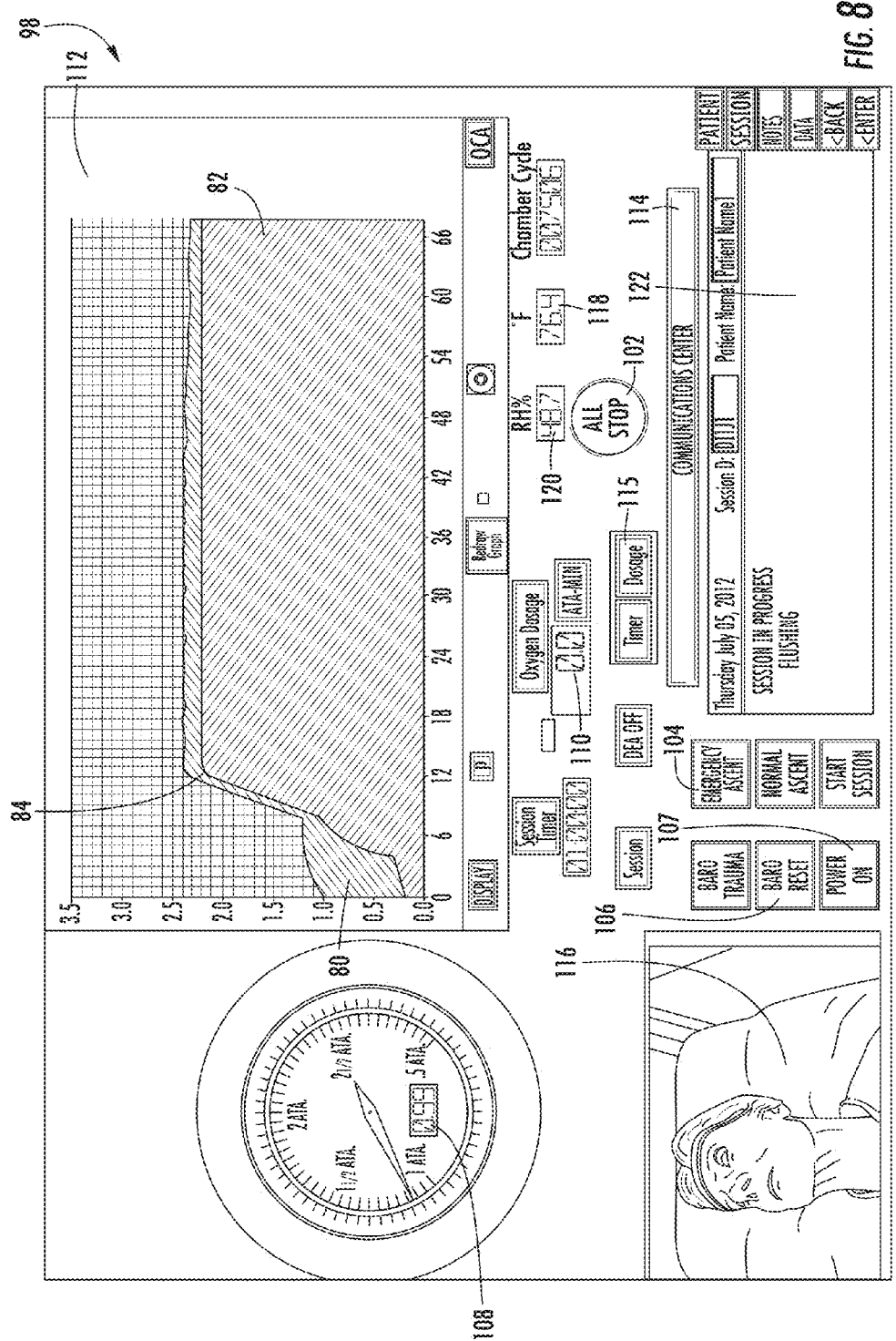
FIG. 8 illustrates an example of an actual chamber session display output, including $pO_2$ content and chamber pressure indications during a treatment session of the present invention.

FIG. 8 illustrates a screenshot of an embodiment of a display of real-time data acquisition. The chamber pressure in ATA is indicated by a first shaded region 80, and the chamber atmosphere $pO_2$ is illustrated by second region 82. The $pO_2$ set-point 84 is 2.2 ATA. The y-axis is session time in minutes.

Figure 9:
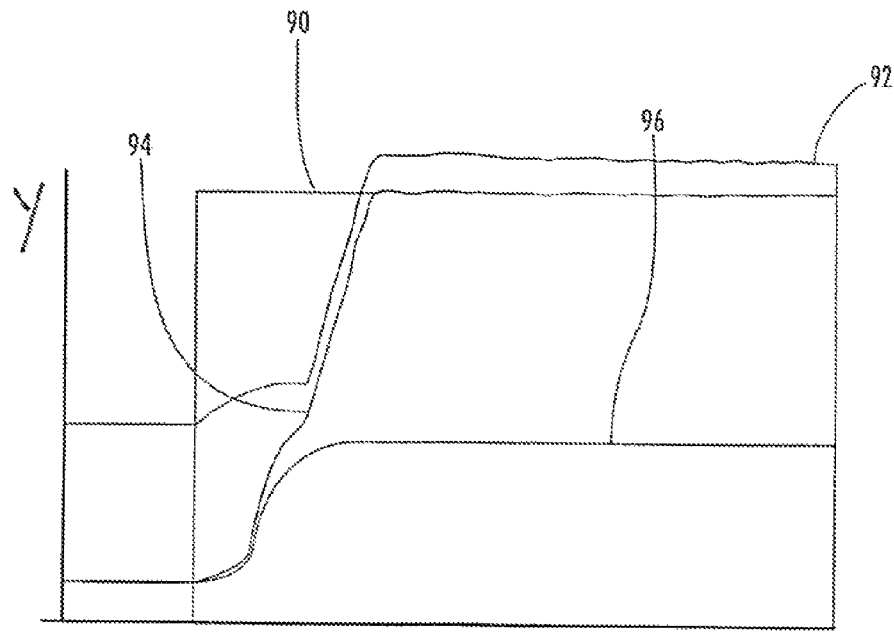
FIG. 9 is a graph illustrating data acquired during a chamber session of the present invention.

FIG. 9 illustrates another embodiment of a display of real-time data acquisition. These measurements of a chamber session indicate that once the chamber door is closed, a true quasi laminar flush with breathing gas is initiated. Oxygen was supplied at the bottom head-end of the chamber and the initial air volume was exhausted at the highest point, feet-end of the chamber to take advantage of the density difference between the oxygen and the air that occupied the chamber before session initiation. A first trace 90 is a horizontal line indicating the $pO_2$ set point. A second trace 92 is the chamber pressure in ATA. A third trace 94 is the chamber $pO_2$ in ATA. A fourth trace 96 is the oxygen concentration by volume. During the flushing phase, the chamber pressure slowly raises to 0.2 ATA. The actual pressurization only starts once the oxygen concentration is at least about 87%. This value can be changed to meet individual, operator's criteria.

Using this method, the actual session starts once curve 94 reaches line 90. This is 17 minutes later than in a conventional, chamber, but the subject is under hyperbaric conditions from the start of the session and is subjected to such conditions for the duration of the session time.

The graph of FIG. 9 also documents that, as $pO_2$ increases due to increases in $O_2$ concentration during the session, the chamber pressure is reduced accordingly.

Given that the $O_2$ concentration is not 100%, the chamber pressure will be higher than 2 ATA, but the $pO_2$ will remain at 2 ATA during the full session time. The computerized controls will reduce the chamber pressure as the oxygen concentration increases during the treatment session to maintain the desired $pO_2$ levels.

If during pressurization a subject feels discomfort due to the pressure increase, a barotrauma switch accessible to the subject from within the chamber may be actuated to alert the chamber operator of the discomfort. Additionally, the computer signals to automatically lower the pressure within the chamber. When the subject indicates it is permissible to continue pressurizations, the rate of pressurization is also reduced. This event is recorded in a subject's file, and following treatment sessions use the slower rate of pressurization by default.

Calculations and readings related to the $pO_2$ are made at several times per second. The $O_2$ dosage is displayed 412 to a chamber operator.

Referring again to FIG. 4, once the session time is reached or the prescribed $O_2$ dosage is achieved 420, the depressurization will automatically start and pressure chamber is gradually relieved 422. The subject/patient is then removed 424 from the chamber 403, and the session is finished.

With continuing reference to FIG. 7, it is illustrated on the graph that once the session time is reached or the requested $O_2$ dosage is achieved, the depressurization will automatically start 79. A prescribing physician has two alternatives: the session can be prescribed as a dosage at a particular $_pO_2$ or conventionally as time and ATA, in which case the unit ATA is referred to as $pO_2$ and not as chamber pressure. In either case, the subject is provided an accurate treatment as desired or prescribed.

Chamber Control

Figure 10:
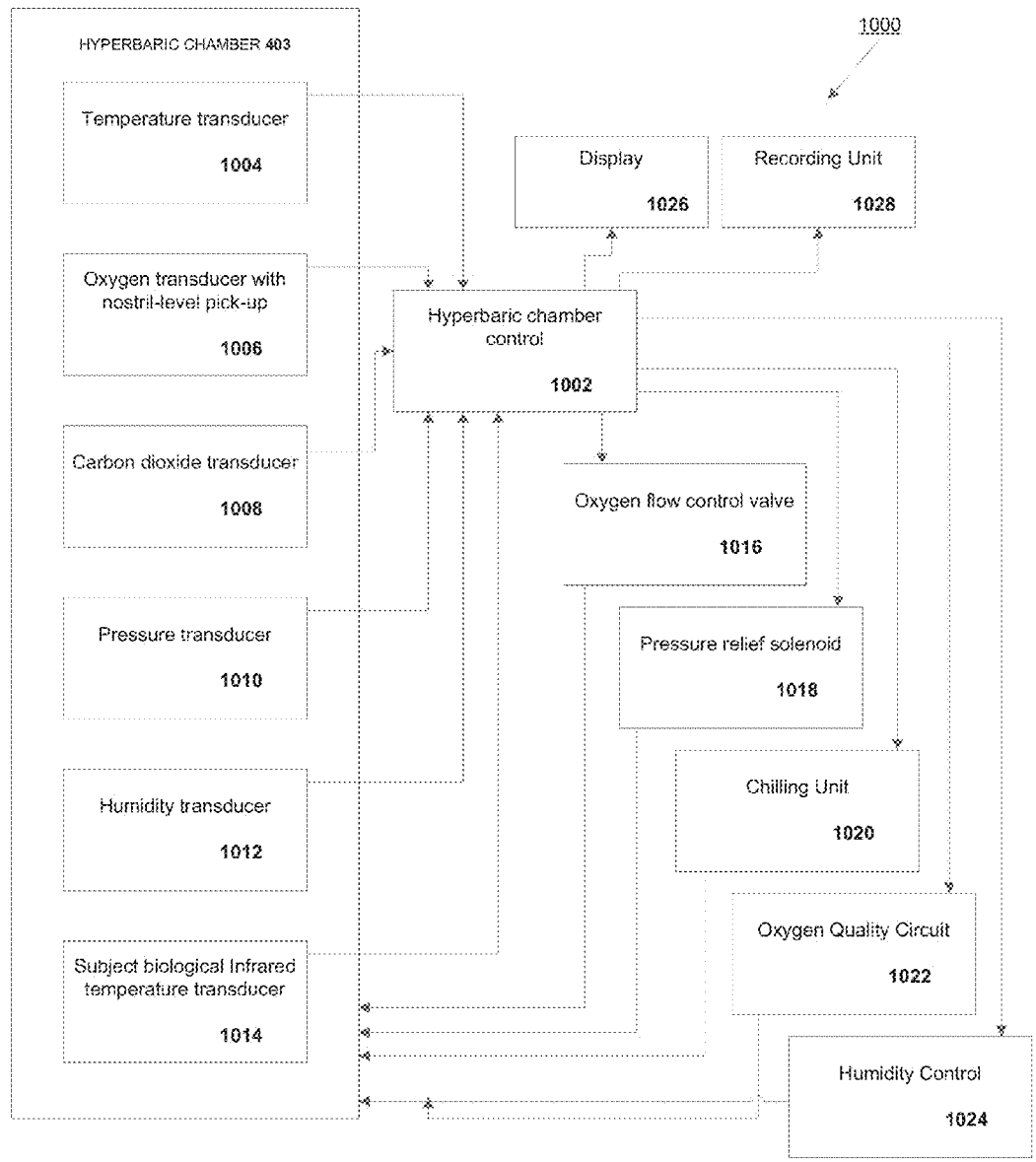
FIG. 10 is a chart illustrating one embodiment of a hyperbaric chamber control system of the present invention.

Referring to FIG. 10, a hyperbaric control, system 1000 is illustrated. A hyperbaric chamber control 1002 is the central processing unit that maintains and adjusts chamber controls and monitors chamber transducers to accurately control a chamber session. The hyperbaric chamber control 1002 is a microcomputer, microprocessor, laptop computer, desktop computer, tablet computing device, mobile device, or any other computing device known in the art. In a preferred embodiment, the chamber control 1002 is a dedicated, stand-alone, real-time microprocessor or microcontroller. In a related embodiment, the chamber control 1002 is accompanied by a secondary computing device having concurrent data collecting capabilities so that system data is redundantly recorded. In the case of a chamber control 1002 failure, the secondary computing device controls the system. Additionally, if the chamber control 1002 recovers after failure, the secondary computing device communicates relevant system data to the chamber control 1002, so that the hyperbaric session continues uninterrupted.

The hyperbaric chamber comprises a plurality of transducers, not limited to: a temperature transducer 1004, an oxygen transducer 1006 that samples oxygen at a subject's nostril level, a $CO_2$ transducer 1008, at least one pressure transducer 1010, and subject biometric transducers such as pulse, EEG, EKG, and infrared temperature transducers 1014. Since the hyperbaric chamber control 1002 comprises a stand-alone processor, a computer that fails to operate ("crashes") does not interrupt the hyperbaric chamber treatment.

These transducers are operated with 5 VDC or 24 VDC and are connected to chamber control 1002 inputs, such as, for example optically insulated digital or analog input modules which operate at 5 VDC. The chamber controls an oxygen flow control valve 1016, pressure relief solenoids 1018, cooling circuits and apparatus 1020, $O_2$ recirculation circuits and apparatus 1022, and humidity control circuits and apparatus 1024. Additionally, the chamber control 1002 outputs information to be displayed on a display device 1026, and records chamber session variables on a recordation device 1028. All control inputs and output states are saved on a real time basis on the controller micro SD and on the HMI PC for redundancy purposes. Backup uninterruptable power supply units ensure function in case of loss of external electrical power.

Conventional, chambers attempt to control, chamber temperature in order to give the subject an acceptable level of comfort. They do this via variations of the chamber venting flow rates. Oxygen, however, is relatively expensive, so to exhaust 90 to 400 liters/min of oxygen is costly. To overcome this problem the current invention contemplates a chamber recirculation/rebreather circuit and apparatus 1022 comprising a scrubber that removes $CO_2$ produced by the subject's metabolism. To facilitate this chamber environment scrubbing, the system additionally comprises a biologic filter that filters 99.9% of bacteria and viruses from the circulating chamber gasses. In one embodiment, there is also at least one particulate and at least one activated carbon filter.

The chamber recirculation circuit and apparatus 1022 comprises a gas circulation device and a scrubber. The scrubber captures moisture and $CO_2$ from the gas mixture within the chamber, and returns "scrubbed" gas back into the chamber. This eliminates the need to ventilate the chamber as an open circuit, and therefore preserves oxygen. Preferably, the $CO_2$ level is maintained below about 500 ppm at 1 ATA, to maintain a desirable subject breathing reflex.

To maintain an atmosphere in the chamber at temperature ideal for treatment, a breathing gas chilling unit 1020 is controlled by a thermostat and the chamber controls 1002. A humidity control/water injection or rejection system is also controlled by the computerized controls 1002, comprising a relative humidity transducer 1012 that maintains chamber relative humidity at pre-set levels at the existing chamber pressure that prevent subject dehydration and increase treatment efficacy, while at the same time reduces risk of electrostatic discharge. These chamber improvements maintain an ideal chamber atmosphere conducive to providing the subject the best treatment outcome, while lowering the cost of treatment due oxygen gas savings.

In one embodiment of the invention, nitrogen gas can be rapidly released into the chamber to act as fire propagation retardant. This automatically occurs in response to sudden increases in temperature. For example, of temperature increase of more than 5° F. be detected in 5 consecutive controller cycles or a pressure increase of more than 3 PSIG be detected during 5 consecutive controller cycles, high oxygen content gas is pushed out of the chamber by $N_2$ supplied into the chamber. After 20 seconds, rapid chamber depressurization is initiated.

Figure 11:
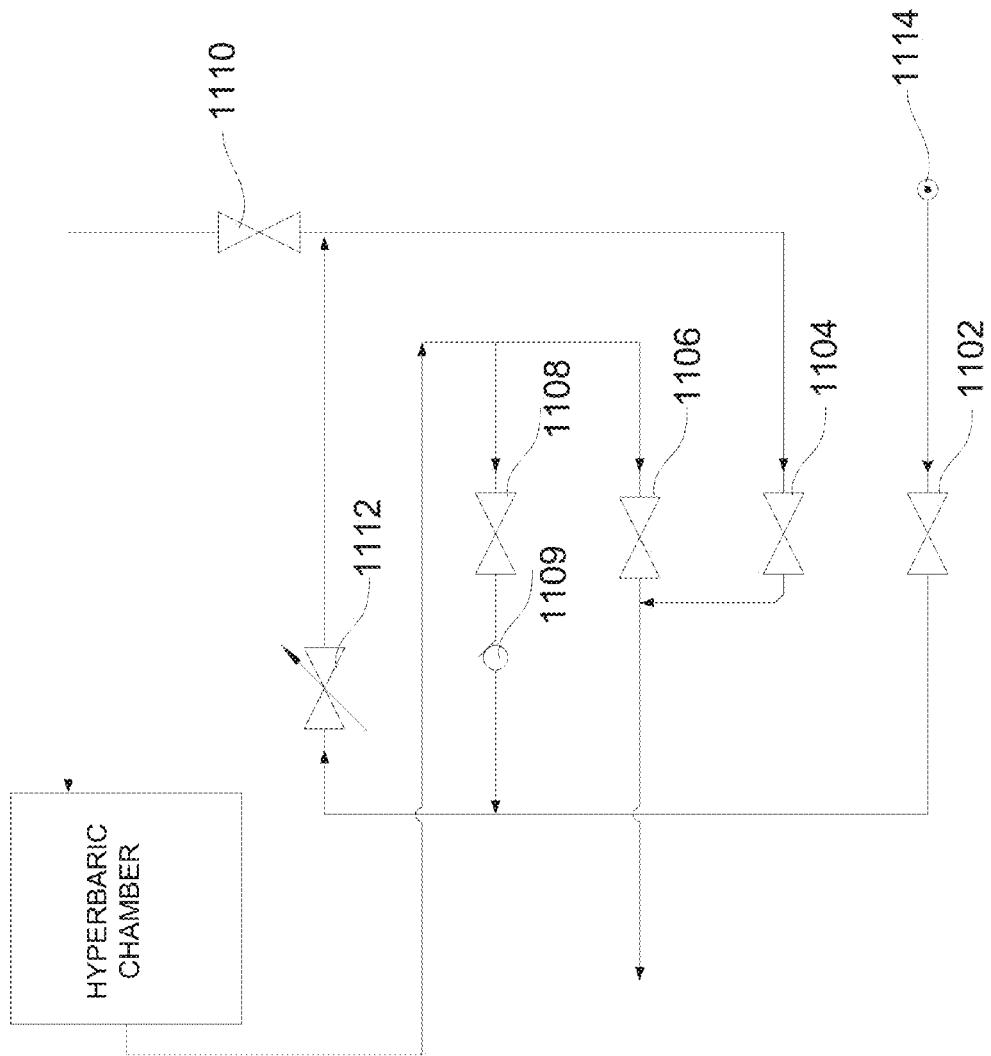
FIG. 11 illustrates one embodiment of gas management hardware.

FIG. 11 illustrates an exemplary configuration of the gas management hardware controlled by the computerized controls 1002. Solenoid valves are opened or closed, and a flow control valve is adjusted to flush, pressurize, maintain pressure, or depressurize the hyperbaric chamber.

To flush the chamber with oxygen, a first solenoid valve 1102 is in an open position, a second solenoid valve 1104 in a closed position, a third solenoid valve 1106 is in an open position fourth solenoid valve 1108 (and associated check valve 1109) are in a closed position, and a fifth solenoid valve 1110 is in an open position. A flow control valve 1112 allows oxygen from an oxygen source 1114 to pass through the first solenoid 1102 a the fifth solenoid 1110 to slowly fill a hyperbaric chamber with oxygen from the bottom of the chamber to the top of the chamber. Air in the chamber is flushed out of a vent proximate the top of the chamber and is exhausted through the third solenoid valve 1106.

With continuing reference to FIG. 11, to pressurize the chamber after it is substantially flushed with oxygen, the third solenoid valve 1106 switched to the closed position, and the flow control valve 1112 is adjusted to alter the rate of pressurization. Once the target oxygen pressure in the chamber atmosphere is reached, the flow control valve 1112 is closed. A proportional integral derivative (PID) controller subsequently adjusts the flow control valve 1112 to maintain the oxygen pressure within about −0.01 ATA and +0.02 ATA of the target pressure.

The depressurization (ascent) stage of a treatment occurs when the second and forth solenoid valves 1104, 1108 are opened, and the fifth valve 1110 is closed. The flow control valve 1112 then regulates the depressurization of the chamber by allowing oxygen to exhaust from the chamber at a desired rate. Once the chamber pressure as low as about 5

PSIG, the third solenoid valve 1106 may be opened to allow the rapid exhausting of oxygen from the chamber.

Turning again to FIG. 8, this figure illustrates a user interface 98 for chamber management. The user interface 98 displays system functions interfaces such as: Body pressurization (e.g. Oxygen body pressurization—with or without air breaks via hood or mask; Air body pressurization and oxygen supply through hood or mask); different pressurization rates with subject active barotrauma control; Premature end of session 102; Emergency end of session 104; Baro re-set button 106; 24 VDC Power button ON/OFF 107; Chamber pressure display; Real time pO2 digital display 108; Real time dosage display 110; Real time graphic display of the chamber session 112 showing $_pO_2$ and chamber absolute pressure; Communications center 114, prompting user to enter pre-determined selection of choices; Means of session data direct entry or via opening either pre-set profile (session) schedules or custom input sessions 115; Video showing subject's face to enable evaluation of subject 116; Information about source gases and system equipment status; Options menu; Temperature display 118; Relative humidity display 120; Session status notification indicator 122; and any other indicator or control known in the art.

Oxygen Management

A healthy breathing human at sea level, will have their hemoglobin saturated with oxygen at 0.29 ATA $pO_2$. The laws of physics (Henry's law) also dictate that the amount of any gas that can be dissolved in a liquid is proportional to its pressure. The human body has two primary means of transporting oxygen to body tissues: First, arterial hemoglobin delivers $O_2$ captured via respiration through the lung's alveoli and capillary beds, and second, the liquid present in the blood, plasma, which primarily delivers oxygen to cells that are not proximate a capillary bed. When breathing air at sea level, arterial oxygen tension is approximately 100 mmHg, and tissue oxygen tension approximately 55 mmHg. Blood hemoglobin basically at saturation levels at surface oxygen pressure, for each hemoglobin molecule can only capture up to four oxygen molecules. Increasing the partial pressure of oxygen does not allow a hemoglobin molecule to carry any additional oxygen. Plasma, however, can dissolve a substantial amount of oxygen under hyperbaric conditions. Under hyperbaric conditions, plasma transfers substantially more oxygen to each individual dell. 100% oxygen at 2 ATA can increase arterial oxygen tensions to 2000 mmHg, and tissue oxygen tensions to around 500 mmHg, allowing delivery of 60 ml oxygen per liter of blood (compared to 3 ml/l at atmospheric pressure). This phenomenon is easily measured in a body's extremities. Increased metabolism due to increased levels of dissolved plasma oxygen creates a temperature increase that is detectable using infrared imaging, which is measured in one embodiment of the present invention. In another embodiment, infrared imaging 1014 is combined with software in order to determine the point in time that defines full, body oxygen saturation in a preferred embodiment, infrared imaging and imaging software communicate with computerized controls 1002 to customize hyperbaric sessions based on full saturation at a given $pO_2$. Additionally, treatment optimization is possible for hyperbaric sessions that are dedicated to treat specific bodily areas, like diabetic extremity gangrenes for example.

The present invention enables a prescribing doctor to exactly determine how long a subject should be submitted to a specified $pO_2$, which is a distinct treatment advantage over what is currently available for an increased level of dosage. The precision and availability of data eliminates currently accepted guess work related to hyperbaric chamber sessions.

Compatibility and Retrofitting

It should be noted that the systems, apparatuses, and methods disclosed herein are adaptable to work in conjunction with any type of oxygen approved for use in hyperbaric oxygen therapies. In all of these instances, chamber sessions are controlled primarily based upon regulating and measuring the $pO_2$.

Not only are newly constructed monoplace hyperbaric chambers amenable to utilizing $pO_2$ as the primary variable for the control of hyperbaric sessions as described herein, regardless of the oxygen source, but existing hyperbaric chambers can easily be converted. This invention therefore contemplates a method of converting an existing hyperbaric chamber that relies on chamber pressure as the primary control variable for the control of a chamber session to a hyperbaric chamber that is controlled primarily based upon regulating and measuring the $pO_2$. To accomplish this, a hyperbaric control system 1000 and any related peripherals (such as infrared imaging 1014 capabilities) are connected to a hyperbaric chamber and the chamber's peripherals necessary for operation. The system 1000 is adaptable for use with gasified liquid oxygen, gaseous oxygen, oxygen enriched air, de-nitrogenated air nitrox, and any other sources of oxygen known in the art. Therefore, existing hyperbaric chambers need not be discarded, for they can be retrofitted with a $pO_2$-based hyperbaric control system 1000.

Besides monoplace hyperbaric chambers, the embodiments described herein are readily adaptable to multiplace hyperbaric chambers. In this case, several subjects can be confined in the same pressurized environment, each subject breathing elevated oxygen gas levels from a full-face mask or hood. Nasal level oxygen pick-up devices (glasses or flex tube, for example) are positioned inside the hood or mask to sample the gas stream. A conduit carries the sampled gas outside of the chamber to an oxygen sensor. These sensor signals will be delivered to a computer located proximate the chamber operator station where a computer monitors and records each subject's inspired oxygen fraction and at the end of the treatment a report is generated for each subject. This system is different than the monoplace system in that it does not directly control the pressure in the chamber, but apprises the operator subject oxygen dosage and alerts the operator if a subject receives inadequate oxygen dosage.

In an alternative embodiment of the invention, a monoplace hyperbaric chamber is pressurized with air, and subject breaths elevated oxygen gas through a full-face mask or hood. Given that chamber flushing is not required, once a subject is in the chamber, pressurization starts at a pre-selected pressurization rate. Simultaneously, oxygen is supplied to the full-face mask or hood at a rate depending on subject need and pressures matching the chamber pressure. This rate is adjustable by the operator. Once the inspired pO2 is reached, the maintenance phase starts as described above in order to maintain the inspired $_pO_2$ at prescription level and this value is use for oxygen exposure calculations. A nasal-level oxygen pick-up device (glasses or flex tube, for example) is positioned inside the hood or mask to sample the gas stream. A conduit carries the sampled gas from the mask or hood to the outside of the chamber to an oxygen sensor. These sensor signals will be delivered to a computer located proximate the chamber operator station where the computer monitors and records the subject's inspired oxygen fraction and at the end of the treatment a report is generated.

Sampling Pickup

Figure 12:
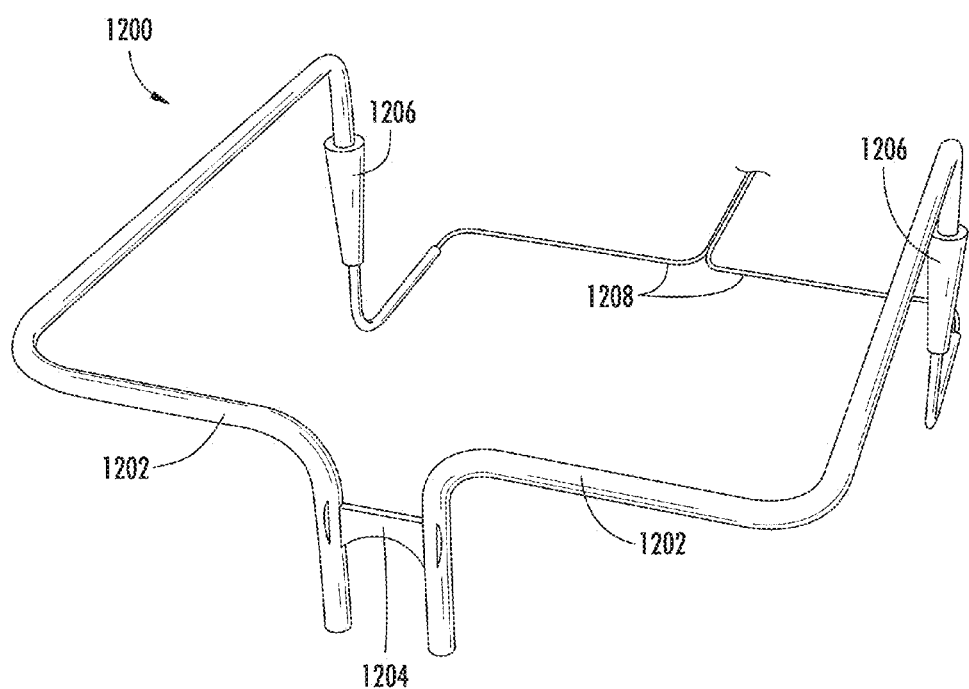
FIG. 12 is an illustration of an isometric view of one embodiment the sample pickup device.

Referring now to FIGS. 12 and 4a, a sample pickup 1200 is designed for being fitted on the head and face of a subject (S) undergoing hyperbaric treatment. The pickup 1200 is designed no continuously collect samples of the hyperbaric atmosphere 413 in order to permit analysis of the concentration and to calculate the $pO_2$ of the atmosphere 413 inhaled by the subject within a monoplace hyperbaric chamber 403.

The pickup 1200 is of a size and dimension proximate that of a typical eyeglass frame or safety glasses frame. The pickup 1200 comprises at least one sample pickup tube 1202 that collects atmospheric samples proximate a subject's (S) nostril height. The pick-up tube 1202 is worn by a subject (S) and is situated as close as possible to the actual media inhaled by the subject (S), yet positioned in a same horizontal plane as the subject (S) nostril level and at a distance to minimize the collection of gasses exhaled by the subject (S).

Additionally, since the pickup 1200 is ideally worn like a pair of glasses, when the subject (S) moves, the sample pickup tube 1202 moves with the subject (S). Therefore atmospheric sampling remains consistent (i.e. the sampling point/s remain/s substantially the same in relation to the subjects nostrils). This pickup 1200 configuration, therefore provides an optimal means to analyze the chamber $O_2$ content, and the ability to calculate the exact $pO_2$ the subject is subjected to and the actual $O_2$ dosage taken by the subject.

FIG. 12 illustrates the pickup 1200 connected to currently available non-collapsing tubing compatible with purified $O_2$, using connecting means known in the art. In one embodiment, sample pickup tubes 1202 are bent to substantially resemble an eyeglass frame. A bridge 1204 connects the sample pickup tubes 1202 to provide structural stability to the pickup, and also provides a surface to contact and rest upon a subject's nose to help keep the pickup 1200 in place and provide a comfortable fit for a subject.

In one embodiment, the pickup tubes 1202 are made from $O_2$-resistant tubing made from at least one of acrylonitrile butadiene styrene, polyolefin, acetal copolymer, cast acrylic tubing, Tygon®, Bev-A-Line®, high density polyethylene, low density polyethylene, ultra high molecular weight polyethylene, fluorinated ethylene propelene, Teflon®, polychlorotrifluoroethylene, polyetheretherketone resin, polyurethane, stainless steel, and any other non-reactive material known in the art.

The pickup tubes 1202 terminate in connectors 1206 that provide a means of connecting the pickup tubes 1202 to at least one transfer tube 1208. The transfer tube 1208 is made from flexible, collapse-resistant, $O_2$-resistant tubing. The proximate end of the transfer tube 1208 sealedly connects to the connectors 1206 on the pickup tubes 1202. The distal end of the transfer tube 1208 connects with at least one sensor (not shown) that aids in atmospheric analysis.

Figure 13:
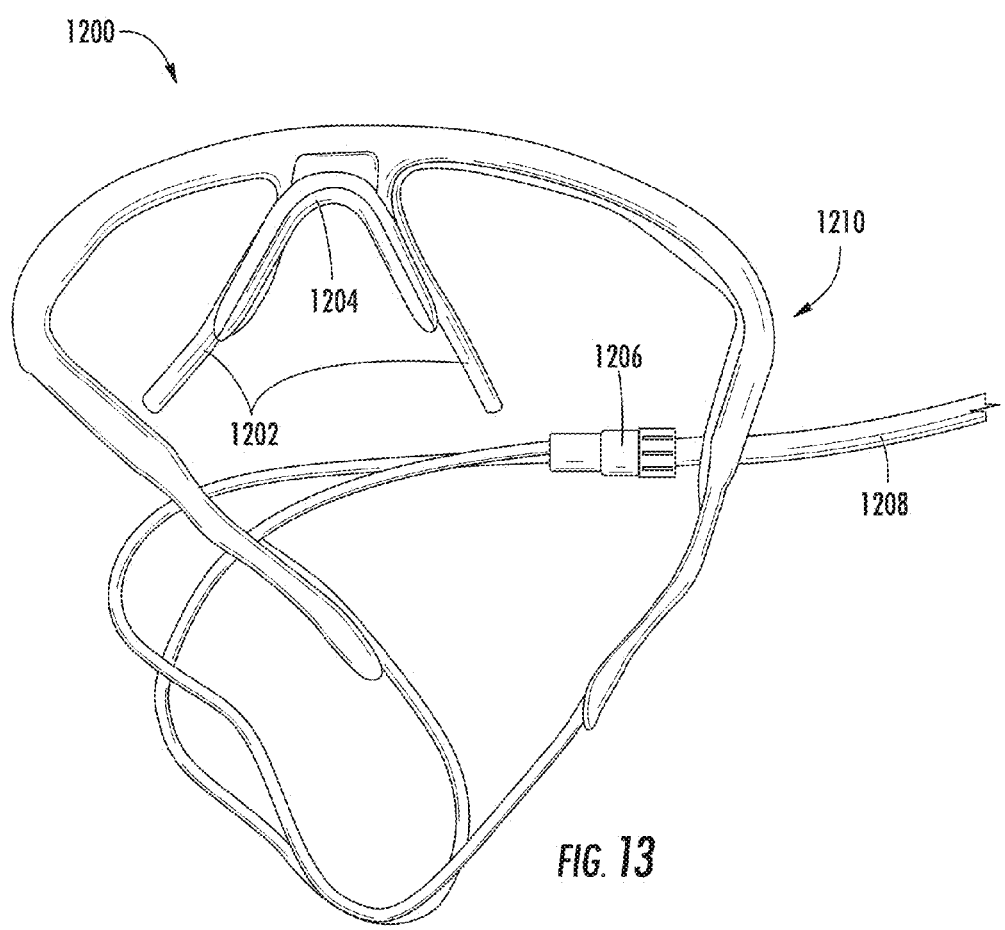
FIG. 13 is an illustration of an alternate embodiment of the sample pickup device.

FIG. 13 illustrates an embodiment of the pickup 1200 wherein an eyeglass-like frame 1210 is used to support sample pickup tubes 1202. The frame 1210 can be manufactured using any moldable or formable $O_2$ compatible material. In particular, the frame 1210 is made from a material chosen from the group comprising high density polyethylene, low density polyethylene, polyethylene terephthalate, polyvinyl chloride, polypropylene, polystyrene, post-consumer resin, K-resin, epoxy resin, phenolic formaldehyde resin, stainless steel, aluminum, and any other material known in the art. The preferred materials for the frame 1210 are $O_2$-compatable polymeric alloys suitable for injection molding.

Noting FIG. 13 again, in a preferred embodiment of the frame 1210, the bridge 1204 is a saddle type bridge 1204 that incorporates a molded nose pad into the bridge 1204.

In a preferred embodiment of the frame 1210, the frame 1210 itself is molded so that frame 1210 integrally comprises the pickup tube 1210. This obviates the need to attach tubing to a frame and minimizes manufacturing cost, yet provides a pickup 1200 that is comfortable for a subject (S) to wear.

Alternatively, in circumstances where a subject's (S) particular facial features restrict the use of frames, pickup tubes 1202 situated near the subject's (S) nostrils can also be placed using malleable or segmented tubing. This type of tubing can be structured to work with non-standard facial topographies so that pickup tubes 1202 remain in the close proximity to the plane of the subject's (S) nostrils. The malleable or segmented tubing can be mounted to eyeglass-like frames, a soft headband, or a hard flexible U-shaped headband.

FIG. 4a illustrates the pickup 1200 being worn by a subject (S) in a hyperbaric chamber 403. The transfer tube 1208 attaches to a junction 415 present in the hyperbaric chamber 403. The junction. 415 allows the transfer tube 1208 to communicate with an external transfer tube 1212, the external transfer tube communicating with hyperbaric chamber controls 1002.

In another embodiment, the transfer tube 1208 directly communicates with the chamber control system. In one embodiment, the pickup tubes 1202 provide hyperbaric chamber 403 atmospheric samples to at least one sensor (not shown).

Figure 14:
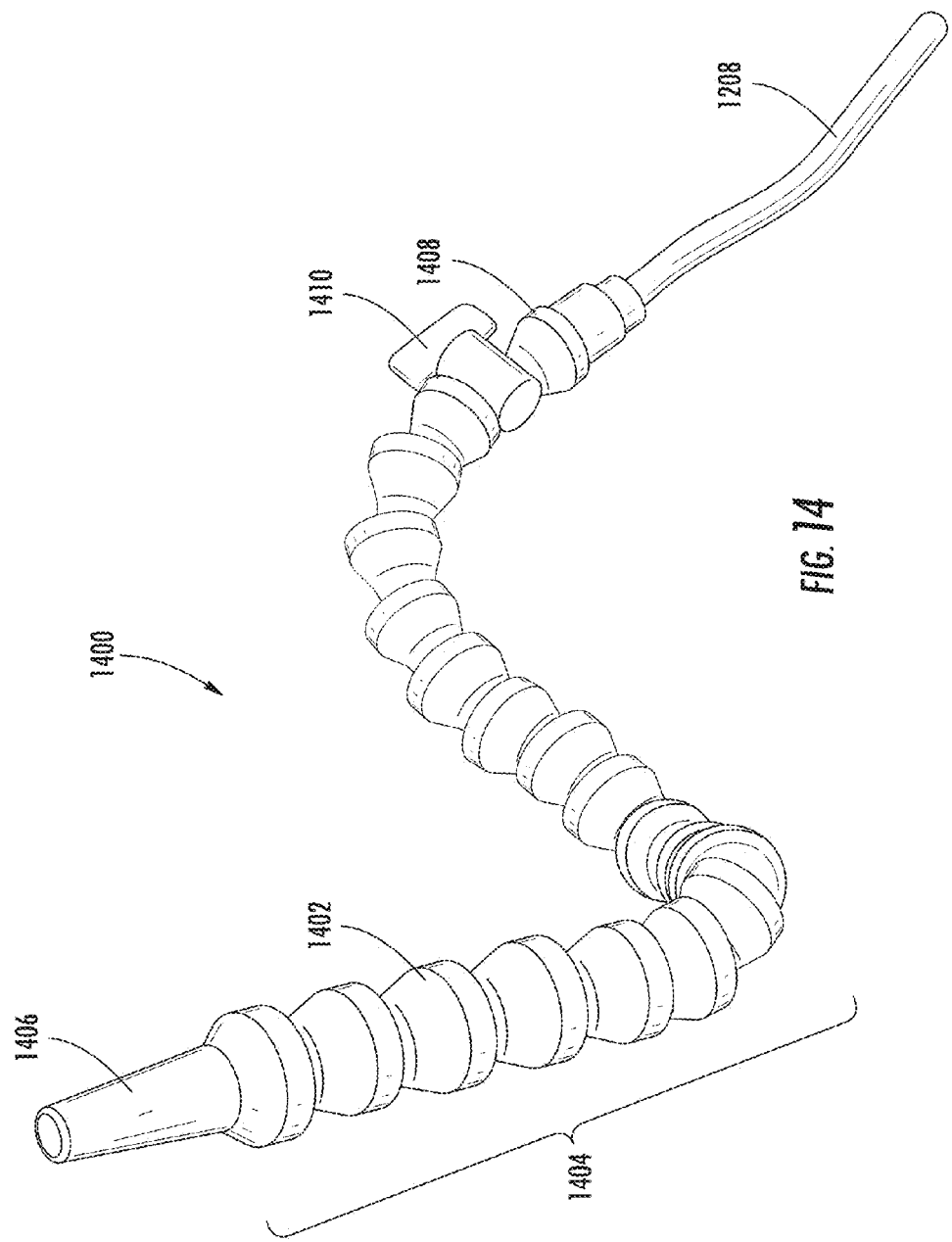
FIG. 14 is an illustration of yet another embodiment of the sample pickup device.

FIG. 14 illustrates an alternative embodiment of a flexible sampling device 1400. In this embodiment, the flexible sampling device 1400 is a series of articulable segments 1402. The segments 1402 sealedly communicate with proximate like segments 1402 to form a sealed hose 1404. The conformation of the hose 1404 is manipulable, yet the hose 1404 statically maintains the conformation into which it is manipulated. A first end of the hose 1404 comprises a nozzle 1406. The nozzle 1406 is the point where atmospheric samples are introduced into the flexible sampling device 1400. At a second end of the hose 1404 is secured an attachment point 1408. In one embodiment of the invention, a valve 1410 is inline with the hose 1404 that regulates the volume of atmosphere sampled by the flexible sampling device 1400. In an alternative embodiment, the hose 1404 need not be segmented, but is bendable to maintain a desired conformation.

Figure 15:
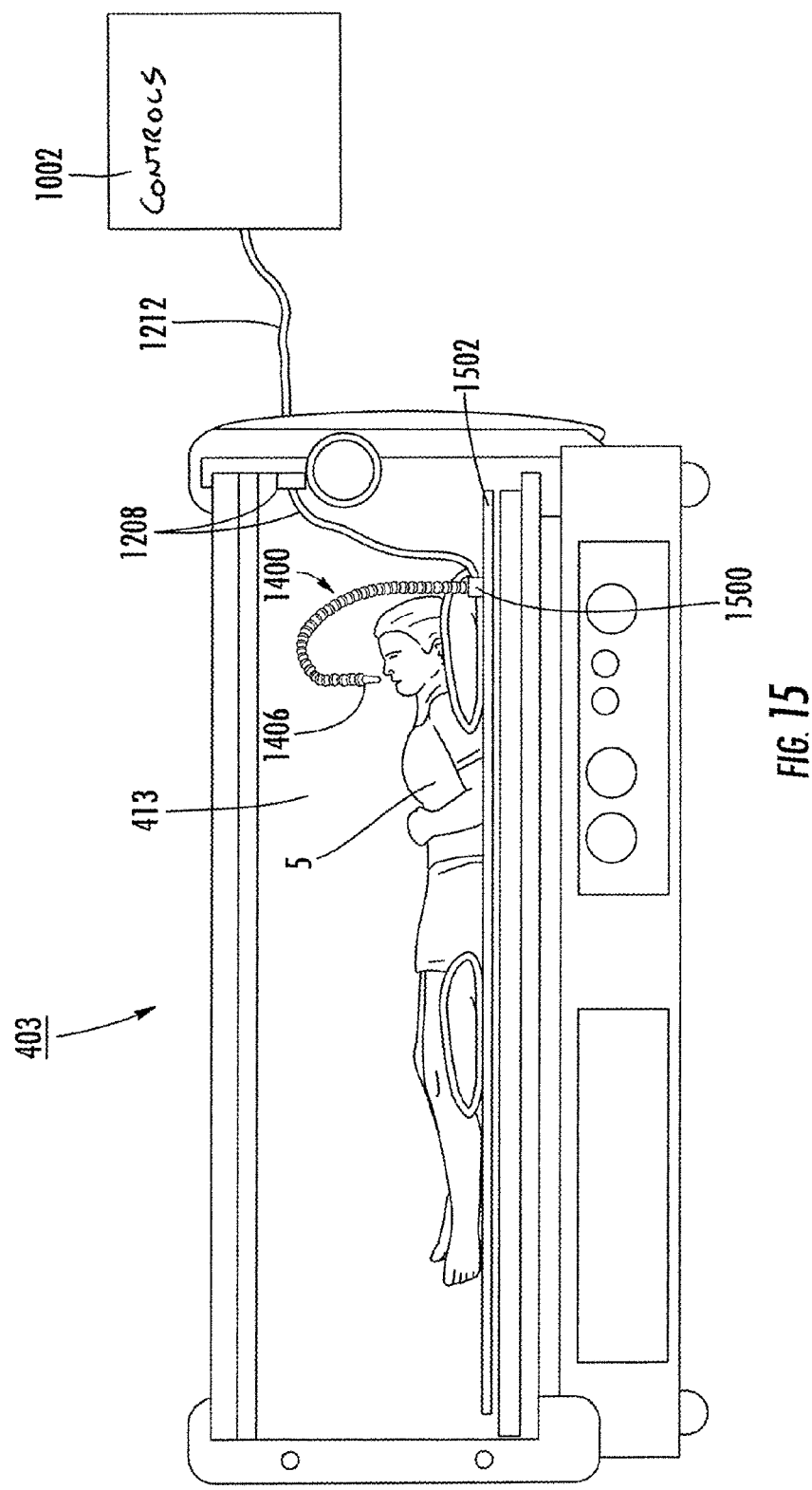
FIG. 15 is an illustration of a side view of the sample pickup device of FIG. 14 in use a subject in a monoplane hyperbaric chamber.

As illustrated by FIG. 15, the flexible sampling device 1400 is attached at an attachment point 1500, preferably on a gurney 1502, that its within a hyperbaric chamber 403. The flexible sampling device 1400 accommodates a subject (S) that has facial deformities, bandage dressings, or other impediments that preclude the use of the eyeglass frame-like like embodiments of contemplated herein (See e.g. FIGS. 12 and 13). In these cases, the subject (8) is most likely sedated, immobile, or asleep. The flexible sampling device 1400 is manipulated so that the nozzle 1406 is placed near a subject's (S) nostrils to sample the atmosphere 413 of the chamber 403 near the nostrils.

A transfer tube 1208 sealedly communicates with the flexible sampling device 1400 through the attachment point 1408. The transfer tube is made from flexible, collapse-resistant, $O_2$-resistant tubing. The proximate end of the transfer tube 1208 sealedly connects to the attachment point 1408, and the distal end of the transfer tube 1208 connects with at least one sensor (not shown) that aids in atmospheric analysis.

The transfer tube 1208 also attaches to a junction 415 present in the hyperbaric chamber 403. The junction 415 allows the transfer tube 1208 to communicate with an external transfer tube 1212, the external transfer tube communicating with the hyperbaric chamber control system 1002.

The invention also contemplates a method of sampling a hyperbaric chamber's atmosphere utilizing the embodiments of the device herein. The invention also contemplates a method of calculating the $pO_2$ a subject is exposed to by measuring the concentration of $O_2$ in a hyperbaric chamber at a subject's nostril level utilizing the embodiments of the device herein.

Many modifications and other embodiments of the invention will come to the mind of one skilled in the art having the benefit of the teachings presented in the foregoing descriptions and the associated drawings. Therefore, it is understood that the invention is not to be limited the specific embodiments disclosed.

Pressure Swing Adsorption

Since liquid oxygen is costly and difficult to safely manage and contain and is also not readily available in many areas where hyperbaric treatments are required, such as seafaring vessels, remote locations, and conflict zones, one embodiment of the present invention utilizes a modified pressure swing adsorption (PSA) device and method to enrich air with oxygen for use in the present embodiments of hyperbaric control.

In one embodiment, a PSA system is used to extract $N_2$ from atmospheric air to provide $O_2$ for the systems, apparatuses, and methods disclosed herein. However, feeding the PSA system, not with air (normoxic nitrox), but instead with DNAX comprising approximately 36% $O_2$ (hyperoxic nitrox) and approximately 64% $N_2$ (other gas traces were left out of consideration because most of them are not affected by the PSA system) $O_2$ is produced with a higher than expected concentration, and/or the cycle time is substantially accelerated.

A PSA system capable of producing 175 SCFH. (standard cubic feet/hour) of 93 to 94% $O_2$ was selected and tested with a fixed amount of CGA Grade E breathing air, using the original controls. The PSA system produced 182 SCF (standard cubic feet) at 94% OEA (oxygen enriched air). Next, this same system was tested in the same conditions as during the previous test, but while feeding the PSA unit with DNAX 36% (De-nitrogenated air nitrox comprising 36% oxygen). The modified system produced 182 SCFH of OEA with an excess of 96% $O_2$ concentration.

In an example trial, a parameter Oxygen Delay was set to 25 seconds. This delay represents a dwell time of the separated gases inside the pressurization tower prior to opening the valve that releases the OEA to an accumulator tank. This time was shortened to 15 seconds, and another test started, feeding the PSA system with DNAX 36% OEA, the same amount of feed gas and the same control settings with the exception of the now reduced Oxygen Delay. The unit produced 294 SCF of OEA with the $O_2$ concentration of 94%.

When the Oxygen Delay was 17 seconds, the result was 283 SCFH with an $O_2$ concentration of 95.3%. Using the same control settings above, the Oxygen Pressure parameter was slightly increased with a result of 280 SCFH OEA with 96%+ concentration. The $O_2$ mix results unexpectedly exceed the ISO specifications for medical grade oxygen enriched breathing air.

By using DNAX OEA/hyperoxic nitrox at the same flow rate and pressure recommended by the manufacturer for air/normoxic nitrox, output was increased by 60% and increased the concentration by 2.13%.

DNAX refers to a process of production of EANx by the use of Hollow Fiber Permeation Membrane System, as patented by Undersea Breathing Systems, Inc. Reference is made to U.S. Pat. Nos. 5,611,845; 5,846,291; 5,865,877; and 5,858,064, the disclosure of which are herein incorporated by reference in their entirety.

What is claimed is:

1. A method for controlling a hyperbaric chamber session comprising the steps of:
   adding oxygen into the chamber from an oxygen source;
   measuring internal pressure of a hyperbaric chamber;
   measuring oxygen concentration in the hyperbaric chamber;
   calculating partial pressure of oxygen in the hyperbaric chamber;
   starting measuring duration of a session when the partial pressure of oxygen in the chamber reached a predetermined level; and
   maintaining the partial pressure of oxygen in the hyperbaric chamber at the predetermined level by adjusting at least one of oxygen flow rate from the oxygen source, the amount of oxygen, carbon dioxide and moisture in the hyperbaric chamber for a predetermined time period.

2. The method for controlling a hyperbaric chamber session of claim 1 further comprising the step of introducing oxygen proximate a bottom region of the hyperbaric chamber and exhausting the hyperbaric chamber proximate a top region of the hyperbaric chamber.

3. The method for controlling a hyperbaric chamber session of claim 2 wherein the oxygen is introduced proximate a subject head-end of the bottom region of the hyperbaric chamber.

4. The method for controlling a hyperbaric chamber session of claim 2 wherein the chamber is exhausted proximate a subject foot-end of the top region of the hyperbaric chamber.

5. The method for controlling a hyperbaric chamber session of claim 1 further comprising the step of calculating total time necessary to provide a subject a prescribed hyperbaric chamber treatment dose.

6. The method for controlling a hyperbaric chamber session of claim 1 further comprising the step of adding oxygen to the hyperbaric chamber.

7. The method for controlling a hyperbaric chamber session of claim 1 further comprising the step of pressurizing the hyperbaric chamber.

8. The method for controlling a hyperbaric chamber session of claim 1 wherein measuring oxygen concentration in the hyperbaric chamber includes measuring the oxygen concentration proximate the subject's nostrils.

9. The method for controlling a hyperbaric chamber session of claim 8, wherein the oxygen concentration proximate the subject's nostrils is measured by using a oxygen pickup tube worn on the face of the subject.

10. The method for controlling a hyperbaric chamber session of claim 8, wherein the oxygen concentration proximate the subject's nostrils is measured by using a flexible oxygen pickup tube positioned proximate the face of the subject.

11. A method of hyperbaric chamber treatment of a subject in need thereof comprising the steps of:
placing the subject in a hyperbaric chamber;
sealing the hyperbaric chamber;
adding oxygen to the hyperbaric chamber from an oxygen source;
measuring pressure of the hyperbaric chamber;
measuring an amount of oxygen in the hyperbaric chamber;
calculating partial pressure of oxygen in the hyperbaric chamber;
pressurizing the hyperbaric chamber;
maintaining the partial pressure of oxygen at a predetermined level by adjusting at least one of oxygen flow rate from the oxygen source, the amount of oxygen, moisture or carbon dioxide in the hyperbaric chamber; and
measuring the time in which the subject is in the hyperbaric chamber at the predetermined partial pressure of oxygen level.

12. The method of hyperbaric chamber treatment of claim 11 wherein the oxygen concentration is measured proximate the subject's nostrils.

13. The method of hyperbaric chamber treatment of claim 11, wherein adding oxygen to the hyperbaric chamber includes introducing oxygen proximate a bottom region of the hyperbaric chamber and exhausting the hyperbaric chamber proximate a top region of the hyperbaric chamber.

14. The method of hyperbaric chamber treatment of claim 13 wherein a timer is used to measure the time in which the subject is in the hyperbaric chamber is started after the air is substantially flushed from the hyperbaric chamber and the chamber reaches the predetermined partial pressure of oxygen level.

15. A hyperbaric chamber system comprising:
a hyperbaric chamber;
a pressure transducer with the hyperbaric chamber for measuring pressure inside the hyperbaric chamber;
an oxygen transducer with the hyperbaric chamber for measuring a concentration of oxygen inside the hyperbaric chamber;
at least one valve with the hyperbaric chamber for regulating the pressure inside the hyperbaric chamber;
a recirculation apparatus for removing carbon dioxide and moisture; and
a hyperbaric chamber control having a central processing unit that calculates partial pressure of oxygen in the hyperbaric chamber, the hyperbaric chamber control receiving input signals from the pressure and oxygen transducers and outputting signals to adjust the valve to maintain the partial pressure of oxygen at a predetermined level.

16. The hyperbaric chamber system of claim 15 further comprising an atmosphere pickup for sampling the oxygen inside the hyperbaric chamber, wherein the pickup is connected to the oxygen transducer.

17. The hyperbaric chamber system of claim 16 wherein the atmosphere pickup is situated proximate a subject's nostrils.

18. The hyperbaric chamber system of claim 17 wherein the atmosphere pickup is shaped like eyeglass frames to engage a subject's face.

19. The hyperbaric chamber system of claim 16 wherein the atmosphere pickup comprises a segmented hose.

20. The hyperbaric chamber system of claim 15 further comprising an inlet proximate a bottom region of the hyperbaric chamber, the inlet for flushing the hyperbaric chamber with oxygen.

21. The hyperbaric chamber system of claim 15 further comprising an outlet proximate a top region of the hyperbaric chamber, the outlet for flushing gas from the hyperbaric chamber.

22. The hyperbaric chamber system of claim 15 further comprising a pressure swing adsorption apparatus to supply purified oxygen to the hyperbaric chamber.

23. The hyperbaric chamber system of claim 22 wherein de-nitrogenated air nitrox is a source gas for the pressure swing adsorption apparatus.

* * * * *